(12) United States Patent
Maeda (10) Patent No.: US 12,416,799 B2
(45) Date of Patent: Sep. 16, 2025

(54) ENDOSCOPE LENS UNIT, ENDOSCOPE, AND MANUFACTURING METHOD OF ENDOSCOPE LENS UNIT

(71) Applicant: OLYMPUS CORPORATION, Tokyo (JP)

(72) Inventor: Kazuya Maeda, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 933 days.

(21) Appl. No.: 17/238,388

(22) Filed: Apr. 23, 2021

(65) Prior Publication Data

US 2021/0255451 A1    Aug. 19, 2021

Related U.S. Application Data (63) Continuation of application No. PCT/JP2018/039623, filed on Oct. 25, 2018.

(51) Int. Cl.
   *G02B 23/24*    (2006.01)
(52) U.S. Cl.
   CPC .................. *G02B 23/243* (2013.01)
(58) Field of Classification Search
   CPC .... G02B 23/243; G02B 7/02; G02B 13/0085; G02B 7/021; G02B 5/208
   See application file for complete search history.

(56) References Cited

U.S. PATENT DOCUMENTS

2012/0008934 A1    1/2012 Kawasaki
2013/0342924 A1 * 12/2013 Matsuno ............ G02B 13/0085
                                                     264/2.6
2017/0059848 A1 *  3/2017 Haraguchi ......... G02B 23/2469
2019/0076002 A1 *  3/2019 Shimohata ............. H04N 23/00
2019/0079280 A1 *  3/2019 Yoshida ............ H01L 27/14618
(Continued)

FOREIGN PATENT DOCUMENTS

EP         2682797 A1    1/2014
JP     2004-258215 A    9/2004
(Continued)

OTHER PUBLICATIONS

International Search Report dated Jan. 22, 2019 issued in PCT/JP2018/039623.

*Primary Examiner* — William R Alexander
*Assistant Examiner* — Mackenzi Waddell
(74) *Attorney, Agent, or Firm* — Scully, Scott, Murphy & Presser, P.C.

(57) ABSTRACT

An endoscope lens unit includes a first optical device which includes a first glass plate including a first side surface, a second optical device which includes a second glass plate including a second side surface having the same external dimension as an external dimension of the first side surface, a spacer which includes a third side surface and which defines a distance between the first glass plate and the second glass plate, and a light shielding resin which covers the first side surface, the second side surface, and the third side surface, at least part of the third side surface being located closer to an optical axis than the first side surface and the second side surface and constituting a bottom of a recess, the first glass plate and the second glass plate defining wall surfaces of the recess, the recess being filled with the light shielding resin.

18 Claims, 9 Drawing Sheets

(56) References Cited

U.S. PATENT DOCUMENTS

2019/0082944 A1* 3/2019 Fujimori ................ A61B 1/005
2019/0090720 A1* 3/2019 Maeda ................... G02B 7/021

FOREIGN PATENT DOCUMENTS

| JP | 2012-18993 A | 1/2012 |
| WO | 2012/117986 A1 | 9/2012 |
| WO | 2017/203592 A1 | 11/2017 |

* cited by examiner

ENDOSCOPE LENS UNIT, ENDOSCOPE, AND MANUFACTURING METHOD OF ENDOSCOPE LENS UNIT

CROSS REFERENCE TO RELATED APPLICATION

This application is a continuation application of PCT/JP2018/039623 filed on Oct. 25, 2018, the entire contents of which are incorporated herein by this reference.

BACKGROUND OF THE INVENTION

1. Field of the Invention

The present invention relates to an endoscope lens unit with a side surface covered with a light shielding resin, an endoscope including the endoscope lens unit with the side surface covered with the light shielding resin, and a manufacturing method of the endoscope lens unit with the side surface covered with the light shielding resin.

2. Description of the Related Art

Making an endoscope lens unit disposed at a distal end portion of an endoscope smaller in diameter is important to achieve a less-invasive endoscope. Further, a side surface of the endoscope lens unit is covered with a light shielding resin to prevent outside light from entering an optical path.

International Publication No. 2017/203592 discloses a lens unit which is a wafer level stacked body as a method for efficiently manufacturing a small-diameter lens unit. The wafer level stacked body is manufactured by cutting a stacked wafer in which a plurality of lens wafers respectively including a plurality of lens devices are stacked. The lens wafer includes a light shielding wall surrounding an optical path of a lens, and further includes a spacer extended from the light shielding wall.

SUMMARY OF THE INVENTION

An endoscope lens unit of an embodiment includes a first optical device which includes as a base, a first glass plate including a first side surface, a second optical device which includes as a base, a second glass plate including a second side surface having the same external dimension in a cross-section orthogonal to an optical axis as an external dimension in a cross-section orthogonal to the optical axis of the first side surface, a spacer which includes a third side surface and which defines a distance between the first glass plate and the second glass plate, and a light shielding resin which covers the first side surface, the second side surface, and the third side surface. At least one of the first optical device or the second optical device is a hybrid lens device including a resin lens made of the same material as a material of the spacer. At least part of the third side surface is located closer to the optical axis than the first side surface and the second side surface and constitutes a bottom of a recess. The first glass plate and the second glass plate define wall surfaces of the recess, and the recess is filled with the light shielding resin.

An endoscope of an embodiment includes an endoscope lens unit, the endoscope lens unit including a first optical device which includes as a base, a first glass plate including a first side surface, a second optical device which includes as a base, a second glass plate including a second side surface having the same external dimension in a cross-section orthogonal to an optical axis as an external dimension in a cross-section orthogonal to the optical axis of the first side surface, a spacer which includes a third side surface and which defines a distance between the first glass plate and the second glass plate, and a light shielding resin which covers the first side surface, the second side surface, and the third side surface. At least one of the first optical device or the second optical device is a hybrid lens device including a resin lens made of the same material as a material of the spacer. At least part of the third side surface is located closer to the optical axis than the first side surface and the second side surface and constitutes a bottom of a recess. The first glass plate and the second glass plate define wall surfaces of the recess, and the recess is filled with the light shielding resin.

A manufacturing method of an endoscope lens unit of an embodiment includes preparing a device wafer by disposing a plurality of first optical devices on a first glass wafer and disposing a plurality of second optical devices on a second glass wafer, at least either one of the first optical devices or the second optical devices being hybrid lens devices each including a resin lens, preparing a stacked wafer in which the first glass wafer and the second glass wafer are stacked in a state where the first glass wafer and the second glass wafer are disposed at a predetermined distance by a spacer which is made of the same material as a material of the resin lens, separating the stacked wafer into a plurality of stacked devices by cutting the stacked wafer, and covering respective cut surfaces of the plurality of stacked devices and a side surface of the spacer which is located closer to an optical axis than the cut surfaces, with a light shielding resin.

DETAILED DESCRIPTION OF THE PREFERRED EMBODIMENTS

<Endoscope>

Figure 1:
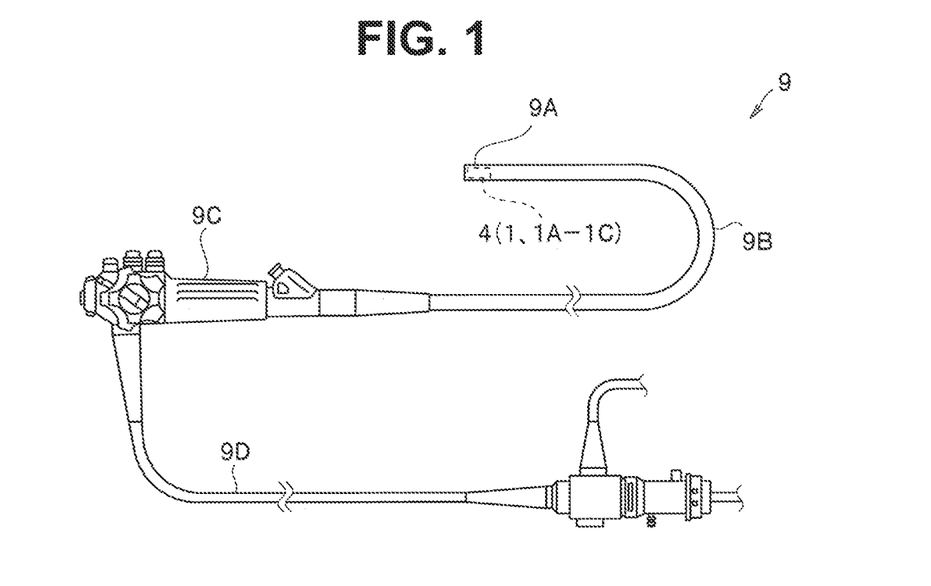
FIG. 1 is a perspective view of an endoscope system including an endoscope of an embodiment.
Figure 2:
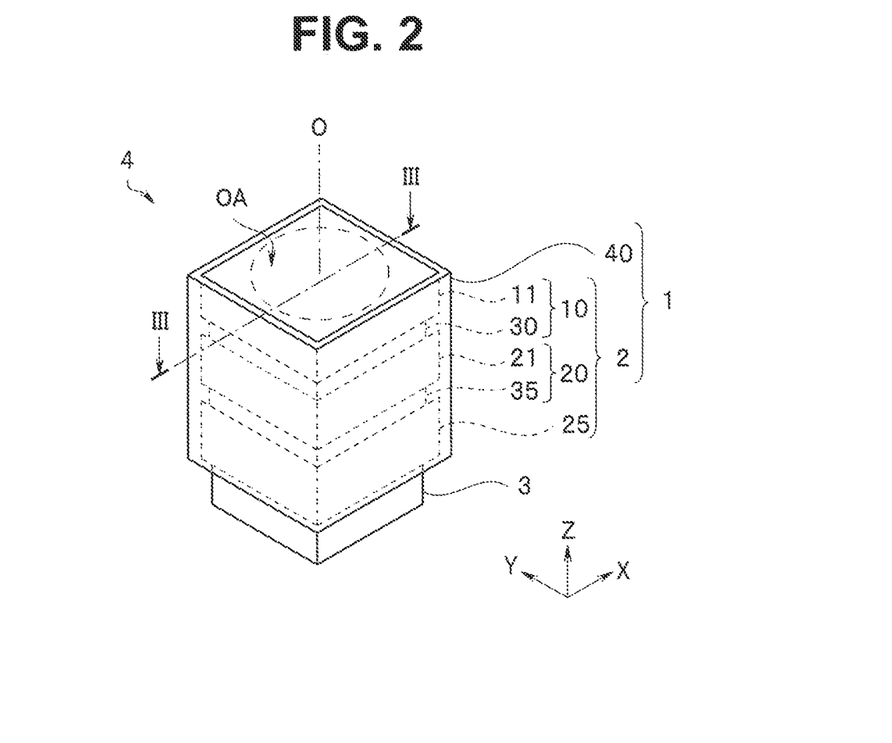
FIG. 2 is a perspective view of a lens unit of the embodiment.

As illustrated in FIG. 1, an endoscope 9 of an embodiment of the present invention includes an insertion portion 9B in which an endoscope lens unit 1 (hereinafter, referred to as a "lens unit") is disposed at a rigid distal end portion 9A, an operation portion 9C disposed at a proximal end side of the insertion portion 9B, and an universal cord 9D extended from the operation portion 9C. The lens unit 1, which is disposed at the distal end portion 9A of the insertion portion 9B of the endoscope 9, forms a subject image on a light receiving surface of an image pickup portion 3. An image pickup signal outputted from the image pickup portion 3 is transmitted to a processor by way of a cable which passes through the universal cord 9D. Further, a drive signal from the processor to the image pickup portion 3 is also transmitted by way of the cable which passes through the universal cord 9D.

As will be described later, the lens unit 1 has a small diameter and can be easily manufactured, so that the endoscope 9 is less invasive and can be easily manufactured.

<Endoscope Lens Unit>

As illustrated in FIG. 2 to FIG. 5, the lens unit 1 of the embodiment includes a first optical device 10, a second optical device 20, a third optical device 25, and a light shielding resin 40. Further, hereinafter, the lens unit 1 in which the light shielding resin 40 is not disposed will be referred to as a stacked device 2.

Note that, in the following description, drawings based on respective embodiments are schematically illustrated, and relationship between a thickness and a width of each portion, a ratio of a thickness and a relative angle of each portion, and the like, are different from real relationship, ratio, relative angle, and the like. The drawings may include portions in which relationship and a ratio of dimensions differ between the drawings. Further, illustration and reference numerals of part of components may be omitted.

Note that the third optical device 25, and the like, are not essential components of the lens unit 1. The lens unit 1 only requires to include at least the first optical device 10, the second optical device 20, the spacer 30, and the light shielding resin 40.

In an image pickup apparatus 4 including the lens unit 1 and the image pickup portion 3, the lens unit 1 forms a subject image on a light receiving portion 3A of the image pickup portion 3.

The image pickup portion 3 is an image pickup device (imager) made of a semiconductor such as silicon. The light receiving portion 3A is a CMOS (complementary metal oxide semiconductor) type semiconductor light receiving circuit or a CCD (charge coupled device). While not illustrated, a plurality of electrodes electrically connected to the light receiving portion 3A are disposed on a back side 3SB of the image pickup portion 3.

The first optical device 10 includes as a base, a first glass plate 11 including a first principal surface 10SA and a second principal surface 10SB on an opposite side of the first principal surface 10SA. The second optical device 20 includes as a base, a second glass plate 21 including a third principal surface 20SA and a fourth principal surface 20SB on an opposite side of the third principal surface 20SA. The third optical device 25 is a third glass plate 25 including a fifth principal surface 25SA and a sixth principal surface 25SB on an opposite side of the fifth principal surface 25SA.

The first optical device 10 (first glass plate 11) is a parallel plate having a rectangular cross section orthogonal to an optical axis O of an optical path OA and includes four first side surfaces 10SS1, 10SS2, 10SS3 and 10SS4. Hereinafter, for example, each of the four first side surfaces 10SS1, 10SS2, 10SS3 and 10SS4 will be referred to as a first side surface 10SS.

As with the first optical device 10, the second optical device 20 (second glass plate 21) includes four second side surfaces 20SS, and the third optical device 25 includes four fourth side surfaces 25SS. Hereinafter, the first side surface 10SS, the second side surface 20SS, and the fourth side surface 25SS will be collectively referred to as a glass side surface.

The glass side surfaces 10SS, 20SS and 25SS are cut surfaces cut at the same time, and thus, have the same external dimension in a cross-section orthogonal to the optical axis O, and are located on the same virtual plane.

The first optical device 10 is a hybrid lens device including a resin lens 30 on the second principal surface 10SB, and an outer circumferential portion of the resin lens 30 also functions as a spacer. In other words, the resin lens 30 which has a spacer function also functions as a spacer 30. The first optical device 10 may include a resin lens and a spacer.

The second optical device 20 is a hybrid lens device including a resin lens 35A and a spacer 35B surrounding the resin lens 35A on the fourth principal surface 20SB. The resin lens 30 is a concave lens, and the resin lens 35A is a convex lens. The third optical device 25 is a glass filter device which removes unnecessary infrared light (for example, light having a wavelength of equal to or greater than 700 nm).

While not illustrated, the lens unit 1 includes components such as an aperture. In other words, the lens unit may employ various configurations in accordance with specifications if the lens unit includes essential components including at least the first optical device 10, the second optical device 20, the spacer 30, and the light shielding resin 40 described above.

Figure 4:
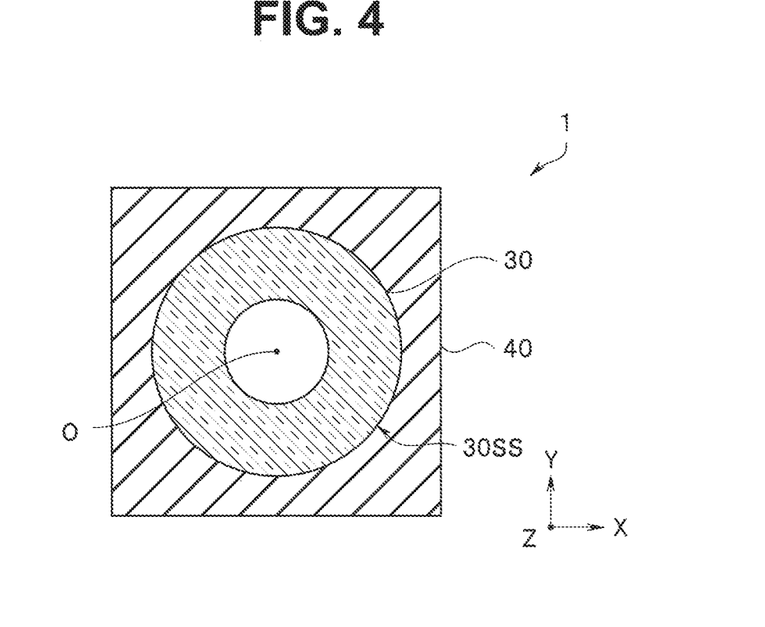
FIG. 4 is a cross-sectional view of the lens unit of the embodiment along a line IV-IV in FIG. 3.

As illustrated in FIG. 4, the resin lens 30 is a concave lens having a circular outer circumference in a cross-section orthogonal to the optical axis O. The outer circumferential portion of the resin lens 30 is a spacer which defines a distance between the first glass plate 11 and the second glass plate 21. In other words, an outer periphery (third side surface 30SS) of the resin lens 30 is a side surface of the spacer.

Figure 3:
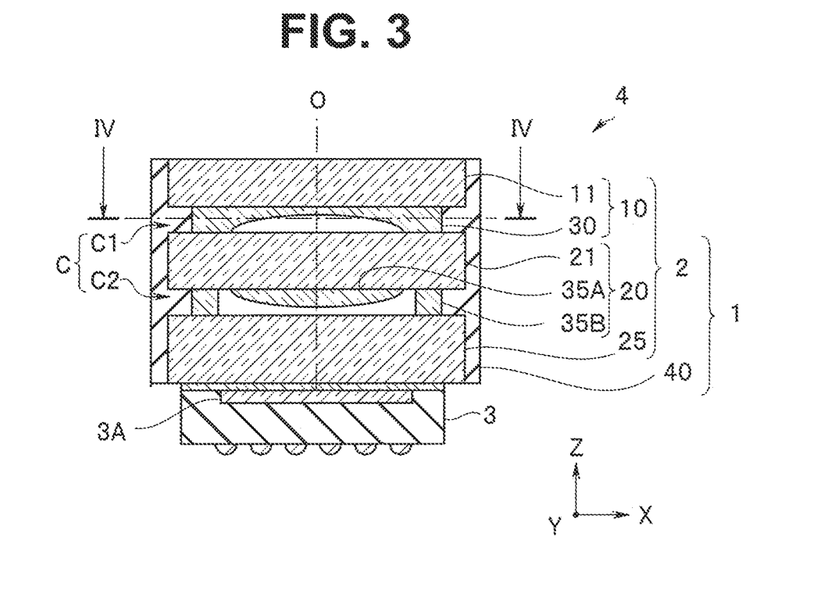
FIG. 3 is a cross-sectional view of the lens unit of the embodiment along a line III-III in FIG. 2.
Figure 5:
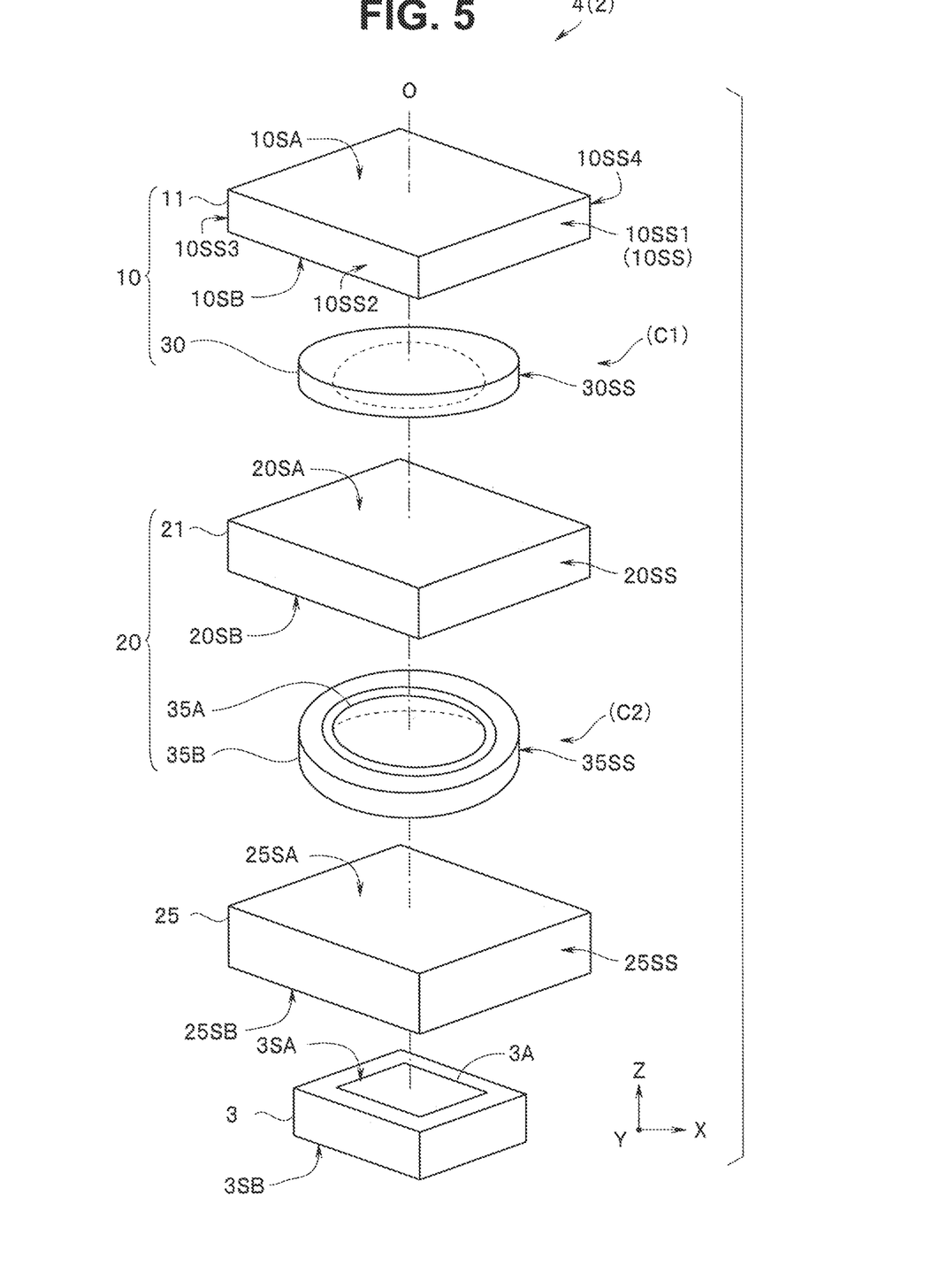
FIG. 5 is an exploded view of a main part of the lens unit of the embodiment.

As illustrated in FIG. 3 and FIG. 5, the third side surface 30SS (spacer side surface) of the resin lens 30 is located closer to the optical axis O than the glass side surfaces 10SS and 20SS and constitutes a bottom of a recess C1 having wall surfaces defined by the second principal surface 10SB of the first glass plate 11 and the third principal surface 20SA of the second glass plate 21. The recess C1 is filled with the light shielding resin 40. An entire surface of the third side surface 30SS is located closer to the optical axis O than the first side surface 10SS, and thus, the entire surface of the third side surface 30SS is covered with the light shielding resin 40. The light shielding resin 40 is a low light transmissive thermoset resin in which light shielding particles are dispersed in an epoxy resin, an acrylic resin, a styrene resin, or the like.

The resin lens 35A is a convex lens having a circular outer circumference in a cross-section orthogonal to the optical axis O. A circular spacer 35B surrounding the resin lens 35A defines a distance between the second glass plate 21 and the third glass plate 25. As will be described later, the resin lens 35A and the spacer 35B are disposed at the same time and are made of the same material. Further, the resin lens 35A and the spacer 35B are made of the same material as a material of the resin lens 30.

The fifth side surface 35SS of the spacer 35B is located closer to the optical axis O than the glass side surfaces 20SS and 25SS and constitutes a bottom of a recess C2 having wall surfaces defined by the fourth principal surface 20SB of the second glass plate 21 and the fifth principal surface 25SA of the third glass plate 25. The recess C2 is filled with the light shielding resin 40.

In the lens unit 1, the light shielding resin 40 is disposed in recesses C (C1, C2) on the side surfaces as well as the glass side surfaces 10SS, 20SS and 25SS of the stacked device 2. There is no possibility that the light shielding resin 40 is detached, so that the lens unit 1 has high reliability.

Note that as will be described later, the glass side surfaces 10SS, 20SS and 25SS are cut surfaces which are cut with an ultrashort pulse laser. The ultrashort pulse laser is a laser for which one pulse is equal to or greater than 100 femtoseconds and equal to or less than 100 picoseconds (subnanoseconds), and thus, has extremely high pulse peak power of equal to or greater than 10 kW and equal to or less than 100000 kW.

In a cutting mechanism using a long pulse laser having a pulse width of equal to or greater than microseconds, division by heat (fusing) or mechanical fracture (scribing) by stress being generated by change of an internal structure is used. In contrast, while a detailed mechanism of cutting using the ultrashort pulse laser is not sufficiently clarified, a cutting margin (scribe width) by cutting is extremely fine from 0.4 μm to 2 μm and dust is not generated. Cutting speed of the ultrashort pulse laser is, for example, 300 m/s in a case of a 2-mm thick glass plate.

Note that it has been impossible to literally specify a structure or properties relating to a difference between the glass side surfaces 10SS, 20SS and 25SS which are cut by the ultrashort pulse laser and cut surfaces by another method and it has been impossible or impractical to analyze and specify such a structure or properties on the basis of measurement.

In other words, even if a shape of the cut surface of the lens unit 1 is measured using a surface roughness meter and an AFM, the shape cannot be distinguished from a shape of a cut surface by a long pulse laser, for example, a $CO_2$ laser. Further, an X ray analysis result of the cut surface of the lens unit 1 cannot be distinguished from a cut surface using a dicing blade.

<Manufacturing Method of Lens Unit>

Figure 6:
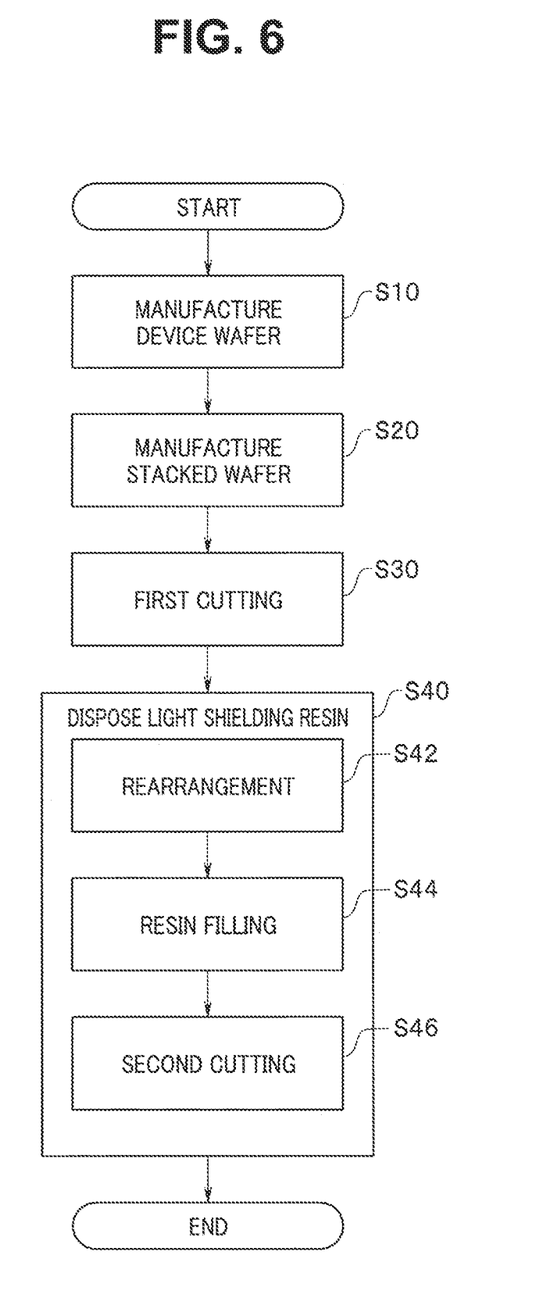
FIG. 6 is a flowchart of a manufacturing method of the lens unit of the embodiment.

A manufacturing method of the lens unit 1 will be described along a flowchart in FIG. 6. The stacked device 2 of the lens unit 1 is a wafer level lens unit which is manufactured by cutting a limited wafer in which a plurality of device wafers respectively including a plurality of optical devices disposed in a matrix are stacked.

<Step S10> Device Wafer Manufacturing Process

Figure 7:
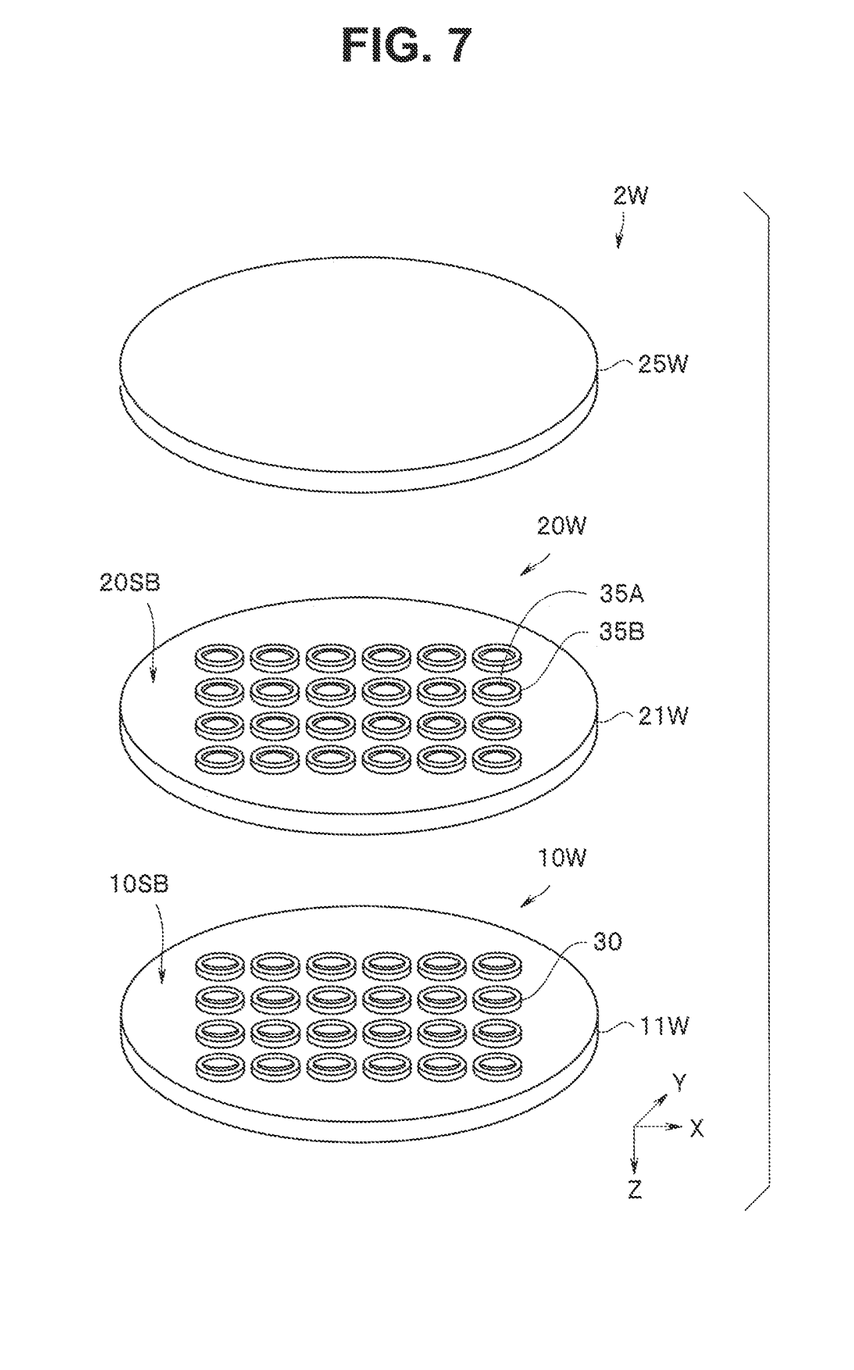
FIG. 7 is a view for explaining the manufacturing method of the lens unit of the embodiment.

As illustrated in FIG. 7, a first device wafer 10W on which a plurality of first optical devices 10 are disposed is manufactured by disposing the resin lens 30 on the second principal surface 10SB of the first glass wafer 11W. An energy curable resin is preferably used as a resin of the resin lens 30.

Cross-linking reaction or polymerization reaction of the energy curable resin proceeds by reception of energy such as heat, ultraviolet ray and electron beam from outside. For example, the energy curable resin includes a transparent ultraviolet curing silicone resin, epoxy resin, or acrylic resin. Note that "transparent" means that a material has less light absorption and less scattering in such a degree that the material is sustainable in use in a use wavelength range.

The energy curable resin is uncured, and thus, manufactured using a mold method which radiates ultraviolet ray to cure the resin in a state where a liquid or gel resin is disposed on the first glass wafer 11W and a mold having a recess having a predetermined inner shape is pressed. Note that silane coupling treatment, or the like, is preferably performed on the glass wafer before the resin is disposed to improve interface adhesive strength between the glass and the resin.

The inner shape of the mold is transferred to an outer shape of the resin lens manufactured using the mold method, and thus, it is possible to easily achieve a configuration having an outer circumferential portion which also functions as a spacer and manufacture an aspherical lens.

A second device wafer 20W is manufactured using the same method as the method for the first device wafer 10W. The resin lens 35A and the spacer 35B of the second device wafer 20W are made of the same resin and are disposed at the same time through molding. Thus, the second device wafer 20W can be easily manufactured.

Note that a convex lens in place of a concave lens may be disposed on the second principal surface 10SB of the first device wafer 10W, and a spacer may be disposed on the third principal surface 20SA of the second device wafer 20W. In other words, the spacer only requires to be disposed at the first glass wafer 11W or the second glass wafer 21W.

<Step S20> Stacked Wafer Manufacturing Process

As illustrated in FIG. 7, the stacked wafer 2W is manufactured by stacking the first glass wafer 11W, the second glass wafer 21W and the third glass wafer 25W at predetermined distances using a plurality of spacers (first optical device 10 and the spacer 35B). The device wafers are bonded using an adhesive agent.

<Step S30> First Cutting Process

Figure 8:
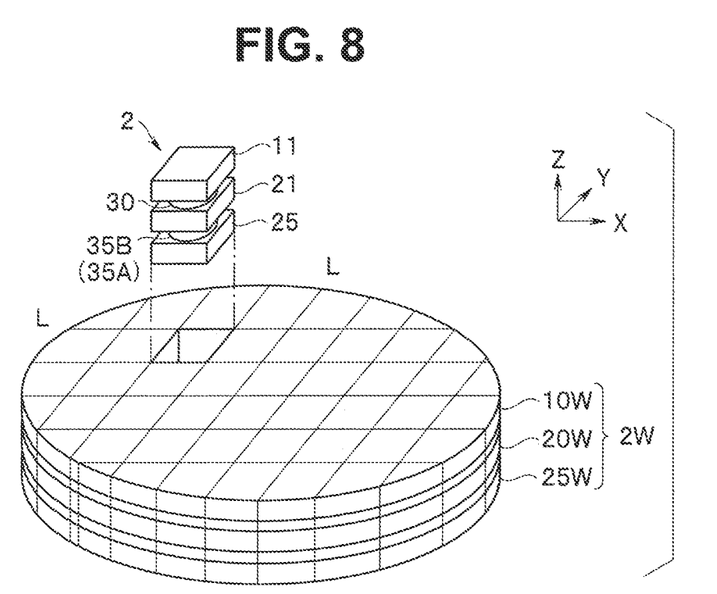
FIG. 8 is a view for explaining the manufacturing method of the lens unit of the embodiment.

As illustrated in FIG. 8, the stacked wafer 2W is separated into a plurality of stacked devices 2 by being cut along a cut line L using the ultrashort pulse laser. For example, a 1.5-mm thick stacked wafer 2W is cut using a 65-watt ultrashort pulse laser having a pulse length of 15 ps and having a wavelength of 1064 nm. Cutting speed is 100 mm/s, a cutting margin (cutting width) is 1 μm, and little dust is generated.

The ultrashort pulse laser can cut a brittle material such as glass but cannot cut an elastic material such as a resin. In other words, the first cutting process is performed using the ultrashort pulse laser which can cut glass but cannot cut a resin. However, the cut line L is set at such a position that a spacer made of a resin is not cut, and thus, the stacked wafer 2W can be cut using the ultrashort pulse laser.

In other words, the cut line L is set at such a position that the first glass wafer 11W, the second glass wafer 21W and the third glass wafer 25W are cut, and a plurality of spacers (the resin lens 30 and the spacer 35B) are not cut. The spacer side surfaces (the side surface of the resin lens 30 and the side surface of the spacer 35B that also function as a spacer) are resin wall surfaces molded in the device wafer manufacturing process.

<Step S40> Light Shielding Resin Disposing Process

In a light shielding resin disposing process S40, the respective cut surfaces of the plurality of stacked devices 2 and the side surfaces of the spacer which are located closer to the optical axis than the cut surfaces are covered with the light shielding resin 40.

In the manufacturing method of the present embodiment, the light shielding resin disposing process S40 includes a rearrangement process S42, a resin filling process S44 and a second cutting process S46.

<Step S42> Rearrangement Process

Figure 9:
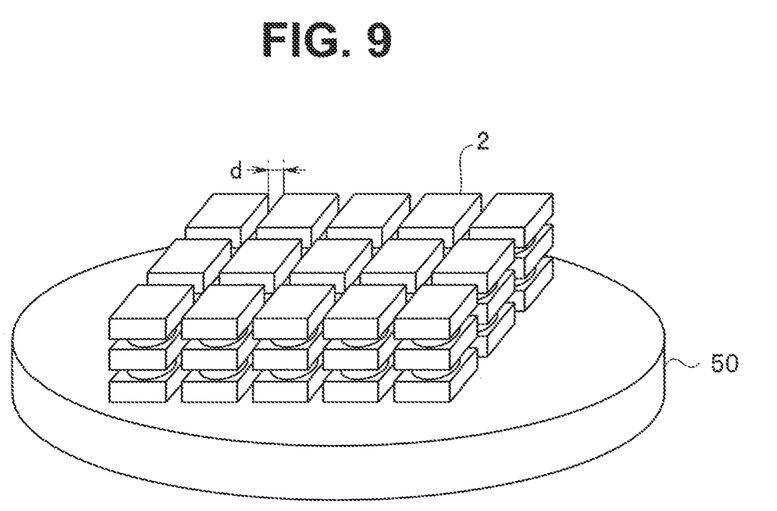
FIG. 9 is a view for explaining the manufacturing method of the lens unit of the embodiment.

As illustrated in FIG. 9, a plurality of stacked devices 2 are disposed on a support wafer 50 which is a support substrate while space having a width d is respectively provided between the stacked devices 2.

<Step S44> Resin Filling Process

Figure 10:
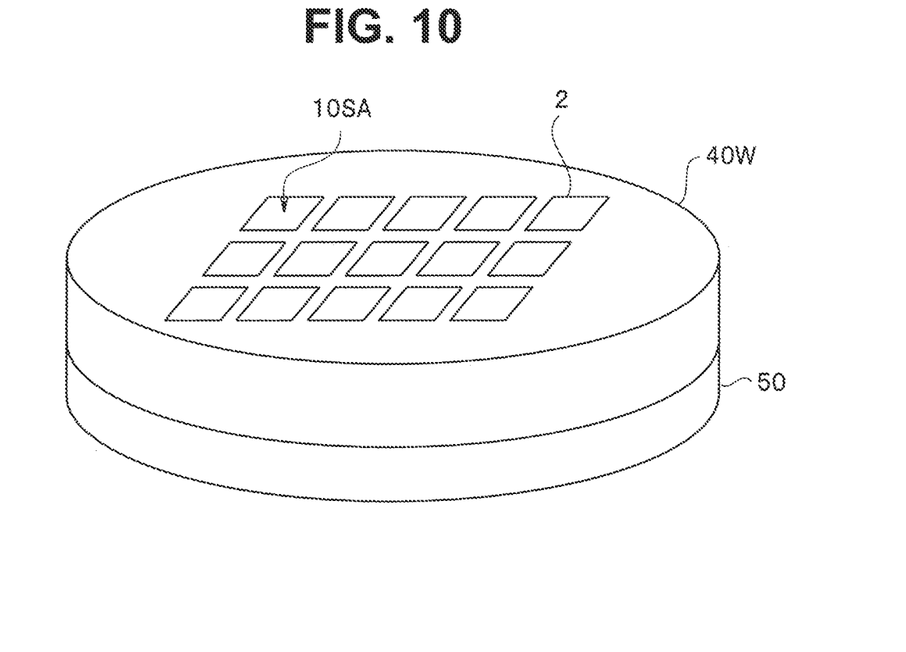
FIG. 10 is a view for explaining the manufacturing method of the lens unit of the embodiment.

As illustrated in FIG. 10, the space between the plurality of stacked devices 2 is filled with the light shielding resin 40W. For example, after the space between the plurality of stacked devices 2 is filled with an uncured light shielding resin 40W using an inkjet method, thermosetting treatment is performed.

Note that in a case where the first principal surface 10SA of the first glass plate 11 is covered with the light shielding resin 40W, CMP (chemical mechanical polishing) processing is performed after the thermosetting treatment.

<Step S46> Second Cutting Process

Figure 11:
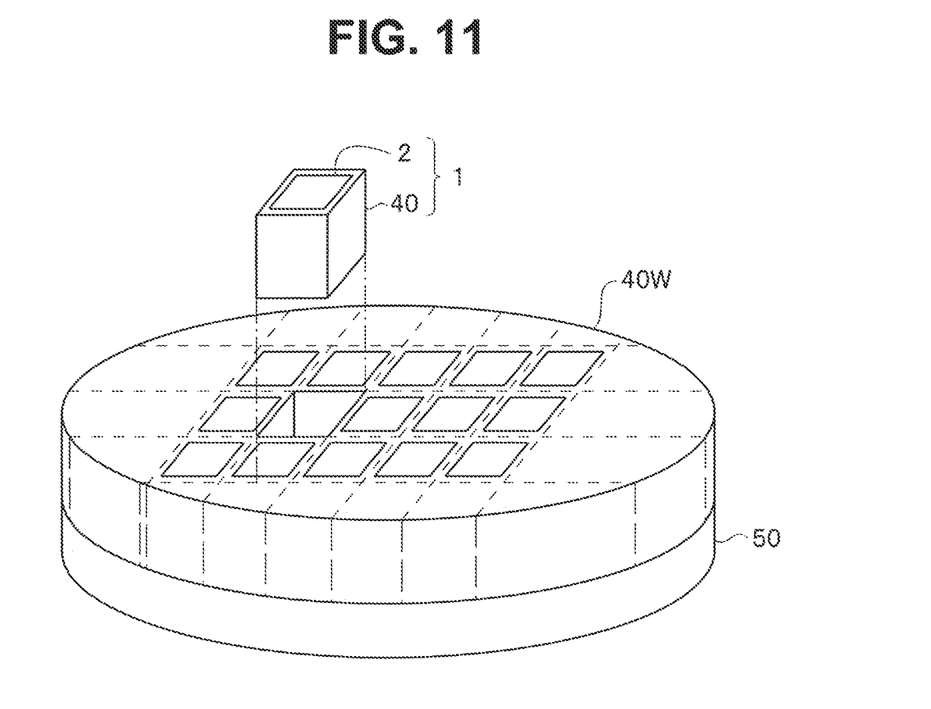
FIG. 11 is a view for explaining the manufacturing method of the lens unit of the embodiment.

As illustrated in FIG. 11, the lens unit 1 including the stacked device 2 with the side surfaces covered with the light shielding resin 40 is manufactured by cutting the support wafer 50 including the plurality of stacked devices 2 along the light shielding resin 40W using a dicing saw and separating the support wafer 50. Note that while the light shielding resin 40 is cut in the second cutting process, the second cutting process may be a so-called half cutting process which only forms a groove on the support wafer 50.

The stacked device 2 including the light shielding resin 40 is manufactured in a wafer level, and thus, the lens unit 1 can be easily manufactured.

Note that the process S40 of disposing the light shielding resin 40 on the side surfaces of the stacked device 2 is not limited to the above-described method in a wafer level. For example, the process S40 may be a process of disposing the light shielding resin 40 on each of the cut stacked devices 2.

Modifications of Embodiment

Lens units 1A to 1C of modifications 1 to 3 of the lens unit 1 of the embodiment will be described next. The lens units 1A to 1C of the modifications are similar to the lens unit 1 and provide the same effects, and thus, the same reference numerals will be assigned to components having the same functions, and description will be omitted.

<Modification 1>

Figure 12:
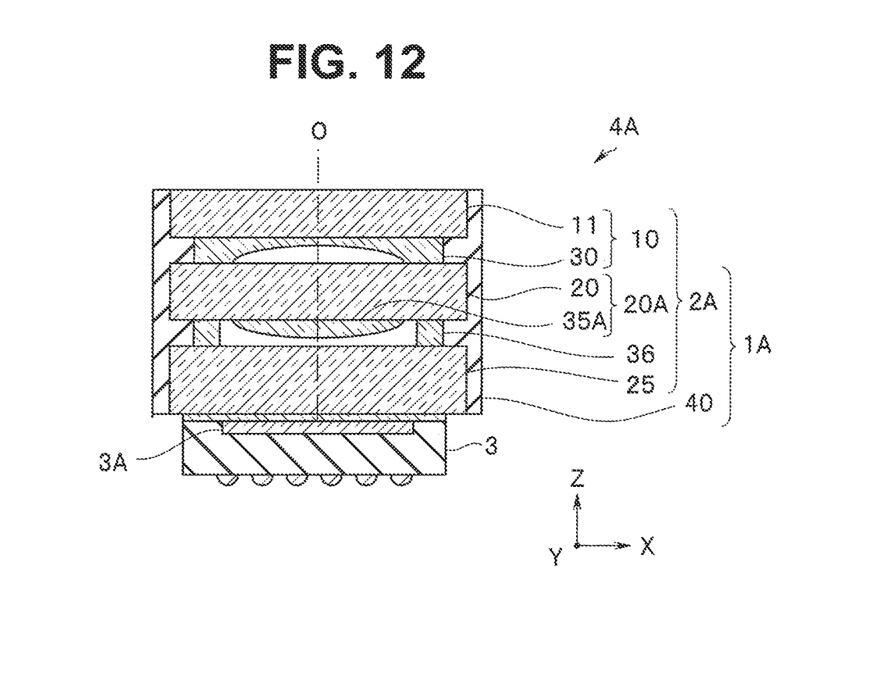
FIG. 12 is a cross-sectional view of a lens unit of modification 1 of the embodiment.

As illustrated in FIG. 12, in the lens unit 1A in modification 1, the spacer 36 is made of, for example, silicon. For example, a silicon wafer is bonded to a glass wafer 25W (not illustrated), and the silicon wafer is processed to a plurality of spacers 36 through etching processing.

In other words, the spacer 36 may be made of the same material as the material of the resin lenses 30 and 35A or may be made of a different material.

<Modification 2>

Figure 13:
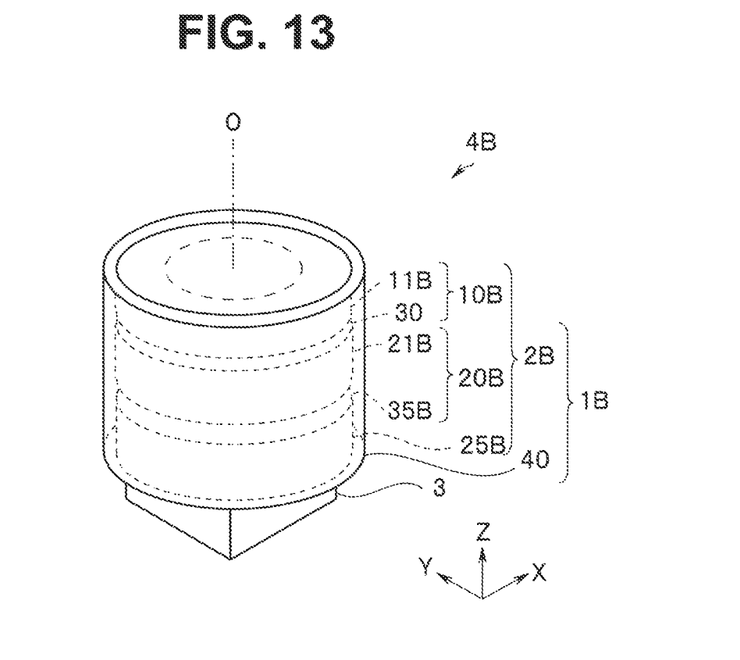
FIG. 13 is a perspective view of a lens unit of modification 2 of the embodiment.

As illustrated in FIG. 13, in the lens unit 1B in modification 2, a plurality of glass side surfaces have circular cross-sections orthogonal to the optical axis.

Processing into a circular shape can be achieved by moving a focal point of the laser in cutting using the ultrashort pulse laser. A cylindrical lens unit 1B obtained by utilizing characteristics of laser processing is particularly small in diameter, so that it is possible to easily achieve a less-invasive endoscope 9.

<Modification 3>

Figure 14:
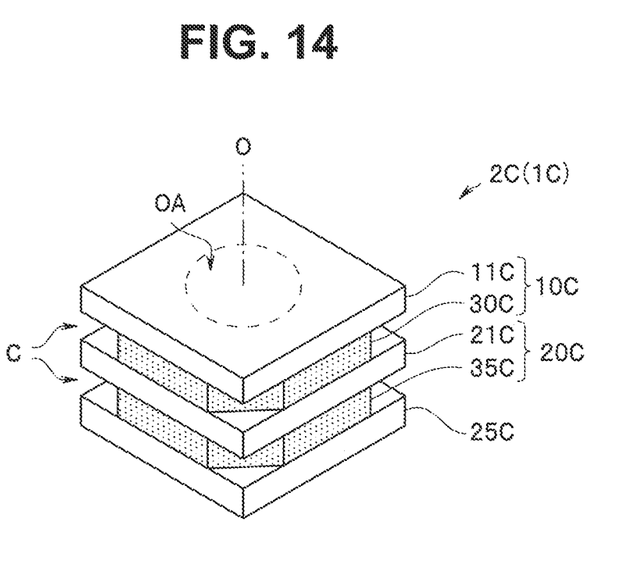
FIG. 14 is a perspective view of a main part of a lens unit of modification 3 of the embodiment.

As illustrated in FIG. 14, in the lens unit 1C in modification 3, part of the spacer side surfaces lies in the same plane as a plurality of glass side surfaces. In other words, part of the spacer side surfaces is located closer to the optical axis than the plurality of glass side surfaces. Note that FIG. 14 does not illustrate a light shielding resin which fills the recess C of the stacked device 2C.

The plurality of glass side surfaces have rectangular cross-sections orthogonal to the optical axis, and the spacer side surfaces have cross-sections orthogonal to the optical axis, in a generally octagonal shape obtained by cutting out four corners of a rectangle.

The recesses C on the side surfaces of the stacked device 2C are also filled with the light shielding resin, so that the lens unit 1C has high adhesion and high reliability. In other words, the lens unit of the embodiment only requires to employ a configuration where at least part of the spacer side surfaces is located closer to the optical axis than the glass side surfaces.

Figure 15:
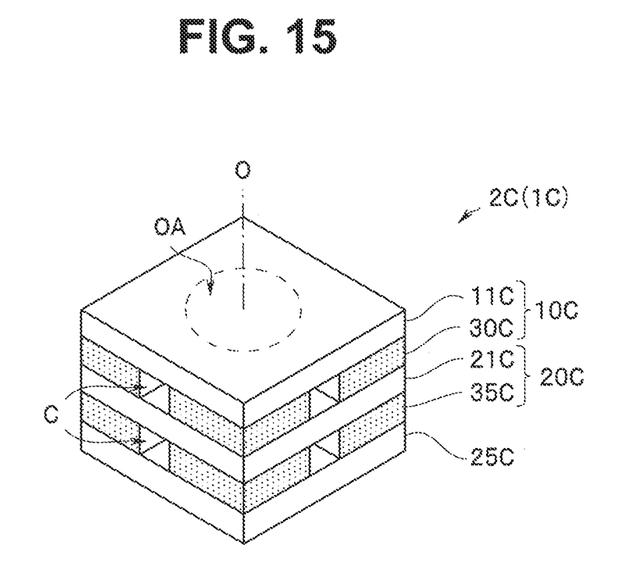
FIG. 15 is a perspective view of the main part of the lens unit of modification 3 of the embodiment.

Note that as illustrated in FIG. 15, cutouts C other than corners of the rectangular spacer side surfaces may be formed. However, cutouts are preferably formed at corners separate from the optical path OA to prevent adverse effects on optical characteristics of the lens unit 1C.

In the lens unit 1C, an ultrashort pulse laser cannot be used in the first cutting process. In other words, it is necessary to cut a spacer made of a resin, and thus, the stacked wafer is cut using a dicing saw, or the like.

In other words, the present invention is not limited to the above-described embodiment, and the like, and various modifications, combinations and application are possible within a range not deviating from the gist of the invention.

What is claimed is:

1. An endoscope lens unit comprising:
   a first glass plate including a first face and a first side surface;
   a second glass plate including a second face opposing the first face and the second glass plate including a second side surface;
   a first resin lens having a single piece construction, the first resin lens being disposed between the first glass plate and the second glass plate, the first resin lens having a first lens face and a second lens face, the first lens face at least indirectly abutting the first face and the second lens face at least indirectly abutting the second face to fix a distance between the first glass plate and the second glass plate, the first resin lens including a third side surface having a thickness in an optical axis direction; and
   a light shielding resin configured to shield light from at least one of the first side surface, the second side surface, and the third side surface;
   wherein
   an entire surface of the third side surface is located closer to an optical axis than each of the first side surface and the second side surface;
   at least part of the third side surface, the first glass plate and the second glass plate together define a recess; and
   the recess being completely filled with the light shielding resin.

2. The endoscope lens unit according to claim 1, wherein the first resin lens is a concave lens.

3. The endoscope lens unit according to claim 1, wherein a first outer periphery of the first glass plate is equal to a second outer periphery of the second glass plate in a plane orthogonal to the optical axis direction.

4. The endoscope lens unit according to claim 1, wherein the first resin lens having an octagonal shape in a cross-section orthogonal to the optical axis.

5. An endoscope comprising:
a lens unit comprising:
- a first glass plate including a first face and a first side surface;
- a second glass plate including a second face opposing the first face and the second glass plate including a second side surface;
- a first resin lens having a single piece construction, the first resin lens being disposed between the first glass plate and the second glass plate, the first resin lens having a first lens face and a second lens face, the first lens face at least indirectly abutting the first face and the second lens face at least indirectly abutting the second face to fix a distance between the first glass plate and the second glass plate, the first resin lens including a third side surface having a thickness in an optical axis direction; and
- a light shielding resin configured to shield light from at least one of the first side surface, the second side surface, and the third side surface;
- wherein
  - an entire surface of the third side surface is located closer to an optical axis than each of the first side surface and the second side surface;
  - at least part of the third side surface, the first glass plate and the second glass plate together define a recess; and
  - the recess being completely filled with the light shielding resin.

6. The endoscope lens unit according claim 1, wherein the first side surface and the second side surface are aligned in the optical axis direction.

7. The endoscope lens unit according claim 1, wherein the thickness is a first thickness, and the recess is a first recess; and
the endoscope lens unit further comprising:
- a third glass plate including a fourth side surface; wherein
- the second glass plate comprises a second resin lens and a spacer having a fifth side surface, the spacer is configured to define a distance between the second glass plate and the third glass plate, the spacer having a second thickness in the optical axis direction;
- the second resin lens is disposed between the second glass plate and the third glass plate;
- at least part of the fifth side surface is located closer to the optical axis than each of the second side surface and the fourth side surface;
- at least part of the fifth side surface, the second glass plate and the third glass plate together define a second recess; and
- the second recess being filled with the light shielding resin.

8. The endoscope lens unit according claim 7, wherein the first resin lens is a concave lens that is concave toward the first glass plate;
the second resin lens is a convex lens that is convex toward the third glass plate.

9. The endoscope lens unit according claim 8, further comprising an image sensor;
wherein the third glass plate is disposed on the image sensor.

10. The endoscope lens unit according claim 7, wherein the third side surface and the fifth side surface are aligned in a direction of the optical axis.

11. The endoscope according to claim 5, wherein an outer circumferential periphery of the first resin lens is configured to define the distance between the first glass plate and the second glass plate.

12. The endoscope according to claim 5, wherein the first resin lens is a concave lens.

13. The endoscope according to claim 5, wherein a first outer periphery of the first glass plate is equal to a second outer periphery of the second glass plate in a plane orthogonal to the optical axis direction.

14. The endoscope lens unit according to claim 1, wherein the thickness is larger than a thickness of the first glass plate and is larger than a thickness of the second glass plate.

15. The endoscope lens unit according to claim 1, wherein the distance between the first face of the first glass plate and the second face of the second glass plate is equal to the thickness.

16. The endoscope lens unit according to claim 1, wherein the first face of the first glass plate directly abuts the first lens face of the first resin lens.

17. The endoscope lens unit according to claim 1, wherein the thickness is equal to the distance between the first and second glass plates.

18. The endoscope lens unit according to claim 1, wherein the first glass plate, the second glass plate and the entirety of the third side surface, together define the recess.

* * * * *